(12) United States Patent
Yu et al.

(10) Patent No.: US 8,086,655 B2
(45) Date of Patent: Dec. 27, 2011

(54) METHODS AND APPARATUS FOR PERTURBING AN EVOLVING DATA STREAM FOR TIME SERIES COMPRESSIBILITY AND PRIVACY

(75) Inventors: Philip Shi-Lung Yu, Chappaqua, NY (US); Spyridon Papadimitriou, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 1138 days.

(21) Appl. No.: 11/855,378

(22) Filed: Sep. 14, 2007

(65) Prior Publication Data
US 2009/0077148 A1    Mar. 19, 2009

(51) Int. Cl.
*G06F 17/14* (2006.01)
(52) U.S. Cl. .................................... 708/400
(58) Field of Classification Search .......... 708/400–409, 708/446
See application file for complete search history.

(56) References Cited

U.S. PATENT DOCUMENTS

| | | | |
|---|---|---|---|
| 6,332,030 B1 * | 12/2001 | Manjunath et al. | 382/100 |
| 6,681,029 B1 * | 1/2004 | Rhoads | 382/100 |
| 7,127,079 B2 * | 10/2006 | Keating et al. | 382/100 |
| 2004/0068399 A1 * | 4/2004 | Ding | 704/200.1 |
| 2007/0239444 A1 * | 10/2007 | Ma | 704/233 |
| 2008/0010671 A1 * | 1/2008 | Mates | 726/4 |
| 2008/0209568 A1 * | 8/2008 | Chang et al. | 726/26 |

OTHER PUBLICATIONS

R. Agrawal et al., "Privacy-Preserving Data Mining," SIGMOD, 2000, 12 pages.
Davis Automotive, "CarChip," http://www.davisnet.com/drive/products/carchip.aso, 2 pages.
W.P. Schiefele et al., "SensorMiner: Tool Kit for Anomaly Detection in Physical Time Series," ACM, Conference, 2004, pp. 1-10.
Y. Zhu et al., "StatStream: Statistical Monitoring of Thousands of Data Streams in Real Time," Proceedings of the 28th VLDB Conference, 2002, 12 pages.
D. Agrawal et al., "On the Design and Quantification of Privacy Preserving Data Mining Algorithms," PODS, 2001, 9 pages.
W. Du et al., "Using Randomized Response Techniques for Privacy-Preserving Data Mining," SIGKDD, Aug. 2003, pp. 1-6.
H. Kargupta et al., "On the Privacy Preserving Properties of Random Data Perturbation Techniques," ICDM, 2003, 8 pages.
Z. Huang et al., "Deriving Private Information from Randomized Data," SIGMOD, Jun. 2005, pp. 37-48.
K. Liu et al., "Random Projection-Based Multiplicative Data Perturbation for Privacy Preserving Distributed Data Mining," IEEE Transactions on Knowledge and Data Engineering, Jan. 2006, pp. 92-106, vol. 18, No. 1.
K. Chen et al., "Privacy Preserving Data Classification with Rotation Perturbation," ICDM, 2005, pp. 1-4.
L. Sweeney, "k-Anonymity: A Model for Protecting Privacy," International Journal on Uncertainty, Fuzziness and Knowledge-based Systems, 2002, pp. 1-14, vol. 10, No. 5.

(Continued)

*Primary Examiner* — David H Malzahn
(74) *Attorney, Agent, or Firm* — William J. Stock; Ryan, Mason & Lewis, LLP

(57) ABSTRACT

Techniques for perturbing an evolving data stream are provided. The evolving data stream is received. An online linear transformation is applied to received values of the evolving data stream generating a plurality of transform coefficients. A plurality of significant transform coefficients are selected from the plurality of transform coefficients. Noise is embedded into each of the plurality of significant transform coefficients, thereby perturbing the evolving data stream. A total noise variance does not exceed a defined noise variance threshold.

17 Claims, 11 Drawing Sheets

| SYM. | DESCRIPTION |
|---|---|
| $x_t$ | TRUE VALUE AT TIME $t$, $1 \leq t \leq N$. |
| $\{x_t\}$ | SET OF ALL VALUES (i.e., SERIES). |
| $N$ | NUMBER OF POINTS (TOTAL OR SO FAR). |
| $n_t$ | PERTURBATION AT TIME $t$. |
| $y_t$ | PUBLISHED VALUE AT TIME $t$, $y_t := x_t + n_t$. |
| $\tilde{y}_t$ | RECONSTRUCTION VIA FILTERING. |
| $\hat{y}_t$ | RECONSTRUCTION VIA LINEAR REGRESSION. |
| $w_{l,t}$ | WAVELET (aka. DETAIL) COEFF. AT LEVEL $l$ AND TIME $t$. |
| $v_{l,t}$ | SCALING (aka. APPROXIMATION) COEFF. AT LEVEL $l$ AND TIME $t$. |
| $\{w_{l,t}\}$ | SET OF ALL WAVELET COEFFICIENTS. |
| $L$ | MAXIMUM WAVELET LEVEL, $L \leq \log_2 N$. |
| $X_k$ | FOURIER COEFFICIENT. |
| $\{X_k\}$ | SET OF ALL FOURIER COEFFICIENTS. |
| $\sigma$ | DISCORD, $\sigma^2 := \text{VAR}[n_t] = E[n_t^2]$. |
| $\tilde{\sigma}$ | UNCERTAINTY AFTER FILTERING, $\tilde{\sigma}^2 := \text{VAR}[\tilde{y}_t - x_t]$. |
| $\hat{\sigma}$ | UNCERTAINTY AFTER REGRESSION, $\hat{\sigma}^2 := \text{VAR}[\hat{y}_t - x_t]$. |
| $K$ | NUMBER OF COEFFICIENTS WITH MAGNITUDE GREATER THAN $\sigma$. |

OTHER PUBLICATIONS

C.C. Aggarwal et al., "A Condensation Approach to Privacy Preserving Data Mining," EDBT, 2004, 18 pages.

E. Bertino et al., "Privacy and Ownership Preserving of Outsourced Medical Data," ICDE, 2005, 12 pages.

A. Machanavajjhala et al., "l-Diversity: Privacy Beyond k-Anonymity," ICDE, 2006, pp. 1-12.

D.L. Donoho et al., "Uncertainty Principles and Signal Recovery," Society for Industrial and Applied Mathematics, Jun. 1989, pp. 906-931, vol. 49, No. 3.

C.C. Aggarwal, "On k-Anonymity and the Curse of Dimensionality," Proceedings of the 31st VLDB Conference, 2005, pp. 901-909.

D.L. Donoho, "Wavelet Shrinkage and W.V.D.: A 10-Minute Tour," International Conference on Wavelets and Applications, Jun. 1992, pp. 1-12.

T. Li et al., "A Survey on Wavelet Applications in Data Mining," SIGKDD Explorations, 2002, pp. 49-68, vol. 4, No. 2.

D.L. Donoho et al., "Adapting to Unknown Smoothness via Wavelet Shrinkage," J. Am. Stat. Soc., Jul. 1994, pp. 1-28, vol. 90.

D.L. Donoho, "De-Noising by Soft-Thresholding," IEEE TOIT, 1995, pp. 1-37, vol. 41, No. 3.

F. Li et al., "Hiding in the Crowd: Privacy Preservation on Evolving Streams through Correlation Tracking," ICDE, 2007, 10 pages.

A. Evfimievski et al., "Limiting Privacy Breaches in Privacy Preserving Data Mining," PODS, Jun. 2003, 12 pages.

D. Kifer et al., "Injecting Utility into Anonymized Datasets," SIGMOD, Jun. 2006, 12 pages.

D.L. Donoho, "Compressed Sensing," IEEE TOIT, Sep. 2004, pp. 1-34, vol. 52, No. 4.

Y. Zhu et al., "Efficient Elastic Burst Detection in Data Streams," SIGKDD, Aug. 2003, 10 pages.

M. Vlachos et al., "Structural Periodic Measures for Time-Series Data," Data Mining and Knowledge Discovery, Feb. 2006, pp. 1-28, vol. 12, No. 1.

E. Keogh, "Time Series Data Mining Archive," University of California, Riverside, Department of Computer Science & Engineering, http://www.cs.ucr.edu/~eamonn/TSDMA/main.php, 2002, 2 pages.

X. Xiao et al., "Personalized Privacy Preservation," SIGMOD, Jun. 2006, 12 pages.

* cited by examiner

FIG. 1

| SYM. | DESCRIPTION |
|---|---|
| $x_t$ <br> $\{x_t\}$ <br> $N$ | TRUE VALUE AT TIME $t$, $1 \leq t \leq N$. <br> SET OF ALL VALUES (i.e., SERIES). <br> NUMBER OF POINTS (TOTAL OR SO FAR). |
| $n_t$ <br> $y_t$ <br> $\tilde{y}_t$ <br> $\hat{y}_t$ | PERTURBATION AT TIME $t$. <br> PUBLISHED VALUE AT TIME $t$, $y_t := x_t + n_t$. <br> RECONSTRUCTION VIA FILTERING. <br> RECONSTRUCTION VIA LINEAR REGRESSION. |
| $w_{l,t}$ <br> $v_{l,t}$ <br> $\{w_{l,t}\}$ <br> $L$ <br> $Xk$ <br> $\{Xk\}$ | WAVELET (aka. DETAIL) COEFF. AT LEVEL $l$ AND TIME $t$. <br> SCALING (aka. APPROXIMATION) COEFF. AT LEVEL $l$ AND TIME $t$. <br> SET OF ALL WAVELET COEFFICIENTS. <br> MAXIMUM WAVELET LEVEL, $L \leq \log_2 N$. <br> FOURIER COEFFICIENT. <br> SET OF ALL FOURIER COEFFICIENTS. |
| $\sigma$ <br> $\tilde{\sigma}$ <br> $\hat{\sigma}$ | DISCORD, $\sigma^2 := \mathrm{VAR}[n_t] = \mathrm{E}[n_t^2]$. <br> UNCERTAINTY AFTER FILTERING, $\tilde{\sigma}^2 := \mathrm{VAR}[\tilde{y}_t - x_t]$. <br> UNCERTAINTY AFTER REGRESSION, $\hat{\sigma}^2 := \mathrm{VAR}[\hat{y}_t - x_t]$. |
| $K$ | NUMBER OF COEFFICIENTS WITH MAGNITUDE GREATER THAN $\sigma$. |

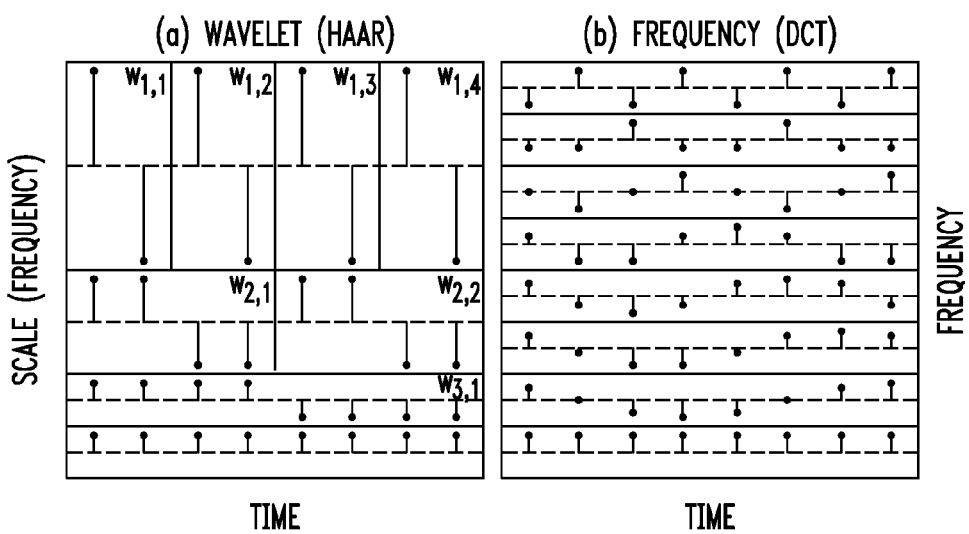

FIG. 2

KNOWLEDGE OF AN ARBITRARY NUMBER OF TRUE VALUES ⟺ KNOWLEDGE OF SIGNAL'S SUBSPACE WITH ARBITRARY PRECISION

⇩  ⇩

COMPLETELY "RANDOM"    COMPLETELY "DETERMINISTIC"

FIG. 6

| ALGORITHM 1 COMPRESSIBLEPERTURBATION($\{x_t\}_{t=1}^N, \sigma$) |
|---|

0  $\{c_i\} \leftarrow$ TRANSFORM($\{x_t\}$)  //Transform coefficients
1  $I \leftarrow \{i : |c_i| \geq \sigma\}$  //Important w.r.t. $\sigma$
2  $p_i \leftarrow \begin{cases} \text{IMPORTANCE}(c_i) & \text{if } i \in I \\ 0 & \text{if } i \notin I \end{cases}$, for all $1 \leq i \leq N$ such that $\sum_i p_i = N^2$
for each coefficient $c_i$ do
  $c'_i \leftarrow$ GAUSSRANDOM($0, \sqrt{p_i}$)  //Perturbation coeffs
  $\{n_t\} \leftarrow$ INVERSETRANSFORM($\{c'_i\}$)  //Perturbation
  $y_t \leftarrow x_t + n_t$, for all $1 \leq t \leq N$  //Published series

FIG. 7

| ALGORITHM 2 FOURIERPERTURB($\{x_t\}_{t=1}^N, \sigma$) |
|---|

$M \leftarrow (N-1)/2$  //Case $N$ odd only, due to space
$\{Xk\} \leftarrow$ FFT($\{x_t\}$)  //Fourier transform
for $k = 1$ to $M$ do
1  $p_k \leftarrow \sqrt{2}|X_{k+1}|$  //All freqs, except DC (i.e., mean value)
  $I \leftarrow \{k : p_k \geq \sigma\}$
  $K \leftarrow 2|I|$  //No. of freqs exceeding $\sigma$
2  $P \leftarrow \sum_{k \in I} p_k^2$
  $v_1 \leftarrow 0$  //Zero DC coeff for perturbation
for $k = 1$ to $M$ do
  if $p_k \geq \sigma$ then
3    $p_k \leftarrow (p_k/P) \cdot (M/K)$
4    $v_{k+1} \leftarrow$ GAUSSRND($0, \frac{\sigma}{2}\sqrt{p_k}$) $+ i$ GAUSSRND($0, \frac{\sigma}{2}\sqrt{p_k}$)
5    $v_{n-k+1} \leftarrow v_{k+1}^*$  //Complex conjugate
  else
    $v_{k+1}$ and $v_{n-k+1} \leftarrow 0$
$\{n_t\} \leftarrow$ INVFFT($\{v_k\}$)  //Inverse FFT (zero DC)
$y_t \leftarrow x_t + n_t$, for all $t$  //Published series

FIG. 8

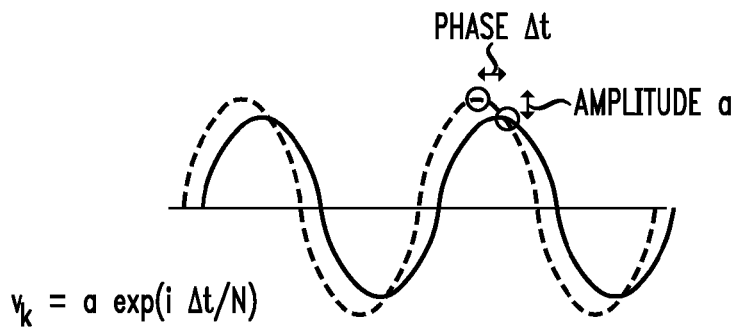

$v_k = a \exp(i \, \Delta t / N)$

FIG. 9

| ALGORITHM 3 WAVELETPERTURB($\{x_t\}_{t=1}^{N}$, $\sigma$) |
|---|
| $\{w_{l,t}\} \leftarrow \text{DWT}(\{x_t\})$ //Wavelet transform (details coeffs) |
| $I_l \leftarrow \{t : |w_{l,t}| \geq \sigma\}$ for each level $l$ |
| 1  $K \leftarrow \sum_l |I_l|$ //No. of coeffs exceeding $\sigma$ |
| $\rho \leftarrow N/K$ //Noise "density" |
| for each detail $w_{l,t}$ do |
| 2    if $t \in I_l$ then //$|w_{l,t}| \geq \sigma$ |
| 3      $w'_{l,t} \leftarrow \text{GAUSSRND}(0, \sigma\sqrt{\rho})$ |
|     else |
| 4      $w'_{l,t} \leftarrow 0$ |
| $\{n_t\} \leftarrow \text{INVDWT}(\{w'_{l,t}\})$ //Inverse DWT (zero smooths) |
| $y_t \leftarrow x_t + n_t$, for all $t$ //Published series |

| DATASET | DESCRIPTION |
|---|---|
| LIGHT | ENVIRONMENTAL SENSOR LIGHT INTENSITIES. |
| CHLORINE | CHLORINE CONCENTRATION IN DRINKABLE WATER. |
| SP500 | STANDARD & POOR'S 500 STOCK INDEX. |

*FIG. 14*
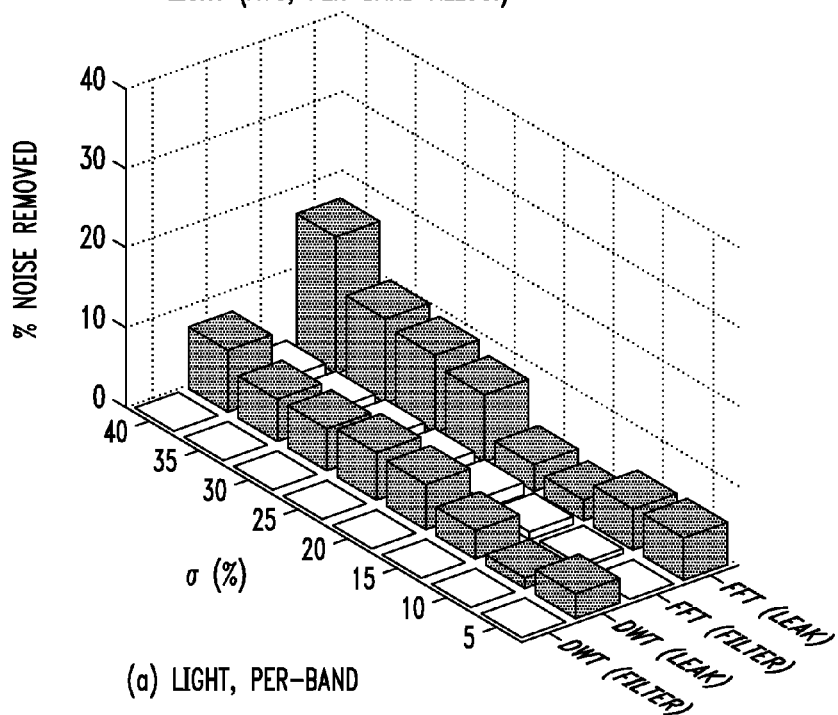
(a) LIGHT, PER-BAND
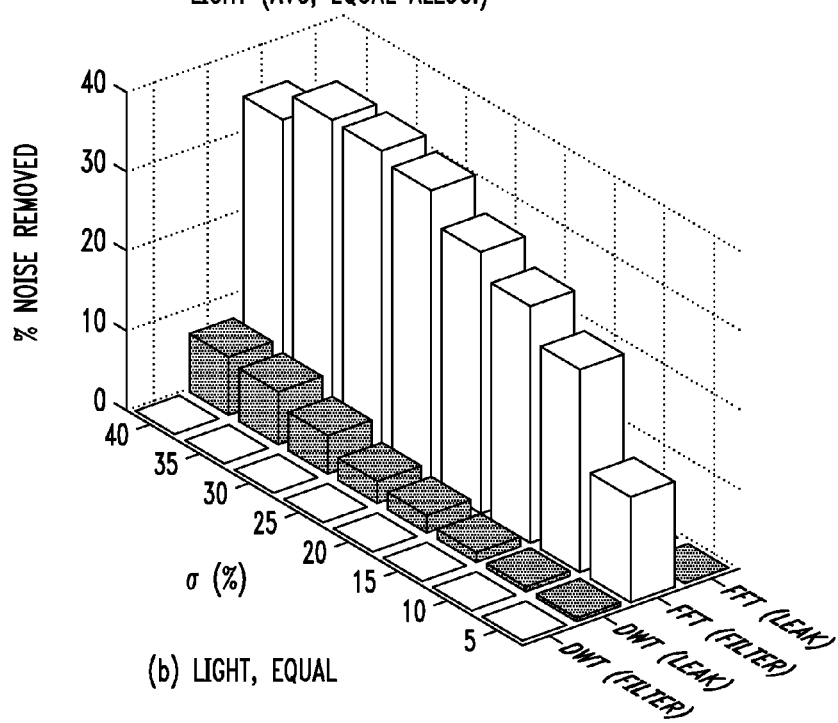
(b) LIGHT, EQUAL

FIG. 15
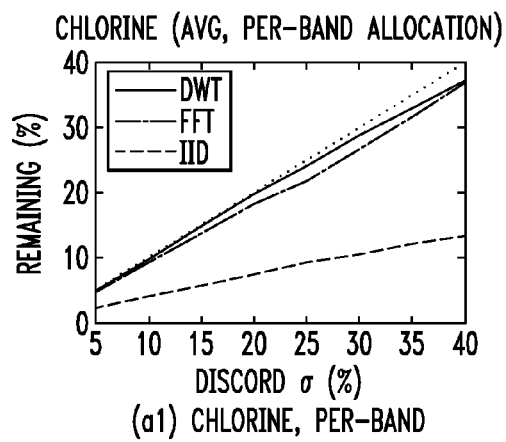
(a1) CHLORINE, PER-BAND
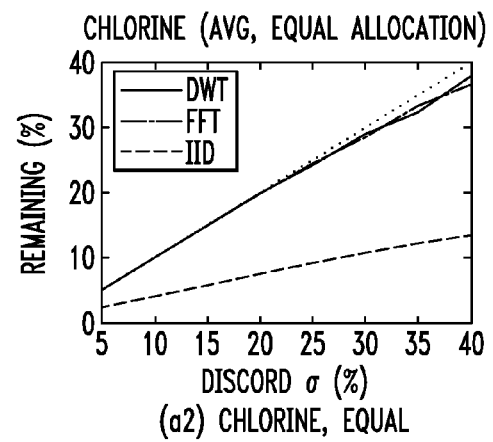
(a2) CHLORINE, EQUAL
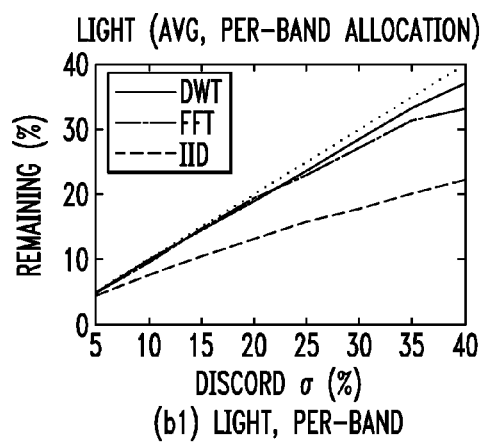
(b1) LIGHT, PER-BAND
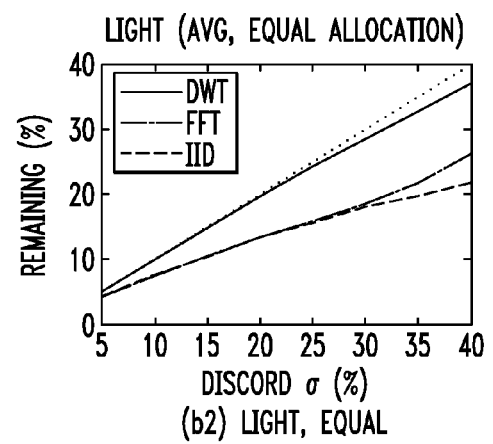
(b2) LIGHT, EQUAL

METHODS AND APPARATUS FOR PERTURBING AN EVOLVING DATA STREAM FOR TIME SERIES COMPRESSIBILITY AND PRIVACY

FIELD OF THE INVENTION

The present invention relates generally to the field of data stream publishing, and more particularly, to data perturbation of data stream values, with application in privacy preservation.

BACKGROUND OF THE INVENTION

Time series data are prevalent in a wide range of domains and applications, such as financial, retail, environmental and process monitoring, defense and health care. Additionally, massive volumes of data from various sources are continuously collected. However, data owners or publishers may not be willing to exactly reveal the true values due to various reasons, most notably privacy considerations. A widely employed and accepted approach for partial information hiding is based on random perturbation. See, for example, R. Agrawal et al., "Privacy Preserving Data Mining," In *SIGMOD*, 2000, which introduces uncertainty about individual values. Consider the following examples:

A driver installing a vehicle monitoring system (see, for example, D. Automotive, "CarChip," http://www.carchip.com/, and W. P. Schiefele et al., "SensorMiner: Tool Kit for Anomaly Detection in Physical Time Series," Technical Report, http://www.interfacecontrol.com/, 2006) may not wish to reveal his exact speed. How can he, for example, avoid revealing small violations of the speed limit (say, by 3-5 mph) but still allow mining of general driving patterns or detection of excessive speeding?

A financial services company may wish to provide a discounted, lower-quality price ticker with a specific level of uncertainty, which is not useful for individual buy/sell decisions but still allows mining of trends and patterns. How can they ensure that the level of uncertainty is indeed as desired?

Similarly, a financial institution (see, for example, Y. Zhu et al., "StatStream: Statistical Monitoring of Thousands of Data Streams in Real Time," In *VLDB*, 2002) may not wish to reveal amounts of individual transactions over time, but still allow mining of trends and patterns. How can they control the level of uncertainty (or, privacy) in the published data and ensure that nothing more can be inferred?

Prior work on numerical and categorical data has focused on the traditional relational model, where each record is a tuple with one or more attributes. Existing methods can be broadly classified into two groups and work (i) either by direct perturbation of individual attributes separately (see, for example, R. Agrawal et al., "Privacy Preserving Data Mining," In *SIGMOD*, 2000; D. Agrawal et al., "On the Design and Quantification of Privacy Preserving Data Mining Algorithms," In *PODS*, 2001; and W. Du et al., "Using Randomized Response Techniques for Privacy-Preserving Data Mining," In *KDD*, 2003) or of entire records independently (see, for example, H. Kargupta et al., "On the Privacy Preserving Properties"; Z. Huang et al., "Deriving Private Information from Randomized Data," In *SIGMOD*, 2005; K. Liu et al., "Random Projection-Based Multiplicative Data Perturbation for Privacy Preserving Distributed Data Mining," *IEEE TKDE*, 18(1), 2006; and K. Chen et al., "Privacy Preserving Data Classification with Rotation Perturbation," In *ICDM*, 2005), (ii) or by effectively swapping or concealing values among an appropriately chosen small group of "neighboring" records (see, for example, L. Sweeney, "k-anonymity: A Model for Protecting Privacy," *IJURKS*, 10(5), 2002; C. C. Aggarwal et al., "A Condensation Approach to Privacy Preserving Data Mining," In *EDBT*, 2004; E. Bertino et al., "Privacy and Ownership Preserving of Outsourced Medical Data," In *ICDE*, 2005; and A. Machanavajjhala et al., "l-diversity: Privacy Beyond k-anonymity," In *ICDE*, 2006).

Although some of the prior work on relational data has considered certain forms of privacy breaches that are possible by exploiting either the global or local structure of the data (see, for example, A. Machanavajjhala et al., "l-diversity: Privacy Beyond k-anonymity," In *ICDE*, 2006; Z. Huang et al., "Deriving Private Information from Randomized Data," In *SIGMOD*, 2005; H. Kargupta et al., "On the Privacy Preserving Properties of Random Data Perturbation Techniques," In *ICDM*, 2003; and K. Chen et al., "Privacy Preserving Data Classification with Rotation Perturbation," In *ICDM*, 2005), the additional aspect of time poses new challenges, some of which are related to fundamental properties of time series (see, for example, D. L. Donoho et al., "Uncertainty Principles and Signal Recovery," *SIAM SIAP*, 49(3), 1989). In particular: (i) sophisticated filtering techniques may potentially reduce uncertainty thereby breaching privacy; (ii) time series can be "described" in a large number of ways (in a sense, a univariate time series is a single point in a very high-dimensional space [see, for example, C. C. Aggarwal, "On k-anonymity and The Curse of Dimensionality," In *VLDB*, 2005]—for example, if the series has 1000 points, there are many 1000-dimensional bases to choose from); (iii) time series characteristics may change over time and, in a streaming setting, new patterns may start emerging in addition to old ones changing (for example, it is not possible to know about quarterly or annual trends while still collecting the first week of data), making both static, global as well as fixed-window analysis unsuitable.

SUMMARY OF THE INVENTION

In accordance with the aforementioned and other objectives, the embodiments of the present invention are directed towards methods and apparatus for data perturbation of data stream values, with application in privacy preservation. The trade-offs between time series compressibility and partial information hiding are examined, as well as their fundamental implications on how uncertainty about individual values by perturbing them should be introduced. More specifically, if the perturbation does not have the same compressibility properties as the original data, then it can be detected and filtered out, reducing uncertainty. Thus, by making the perturbation "similar" to the original data, the structure of the data can be preserved better and breaches are made more difficult. However, as data become more compressible, a fraction of overall uncertainty can be removed if true values are leaked, revealing how they were perturbed. These notions are formalized, the above trade-offs on real data are studied, and practical schemes which strike a good balance and can also be extended for on-the-fly data hiding in a streaming environment are developed.

For example, in one aspect of the present invention, techniques for perturbing an evolving data stream are provided. The evolving data stream is received. An online linear transformation is applied to received values of the evolving data stream generating a plurality of transform coefficients. A plurality of significant transform coefficients are selected from the plurality of transform coefficients. Noise is embedded into each of the plurality of significant transform coefficients, thereby perturbing the evolving data stream. A total noise variance does not exceed a defined noise variance threshold.

In additional embodiments of the present invention the online linear transformation may be a Fourier transform or a wavelet transform. The defined noise variance threshold may be predetermined by at least one of a user and application requirements. The noise may be additively embedded or random. The plurality of significant transform coefficients may include transform coefficients that have an absolute magnitude exceeding a defined threshold. The noise may be embedded into each significant transform coefficient in proportion to a magnitude of each significant transform coefficient.

In further aspects of the present invention and apparatus for perturbing an evolving data stream is provided as well as a method for making a computer implemented process to enable perturbing of an evolving data stream.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 1 is a table providing the main notation necessary for a background on wavelets and filtering, according to an embodiment of the present invention;

FIGS. 2a and b are a series of diagrams illustrating time-frequency properties, according to an embodiment of the present invention;

FIG. 6 is a chart illustrating the general steps (S0-2) for compressible perturbation, according to an embodiment of the present invention;

FIG. 7 is a chart illustrating the steps for pure frequency perturbation or compressible perturbation, using the Fourier representation, which decomposes the series into pure sinusoids, according to an embodiment of the present invention;

FIG. 8 is a graph illustrating lines 4-5 of FIG. 6, according to an embodiment of the present invention;

FIG. 9 is a chart illustrating the steps of time/frequency compressible perturbation using the wavelet transform, according to an embodiment of the present invention;

FIG. 14 is a diagram illustrating noise allocation for light, according to an embodiment of the present invention;

FIG. 15 is a series of diagrams illustrating per-band weighting versus equal allocation for noise allocation, according to and embodiment of the present invention;

DETAILED DESCRIPTION OF PREFERRED EMBODIMENTS

Figure 3:
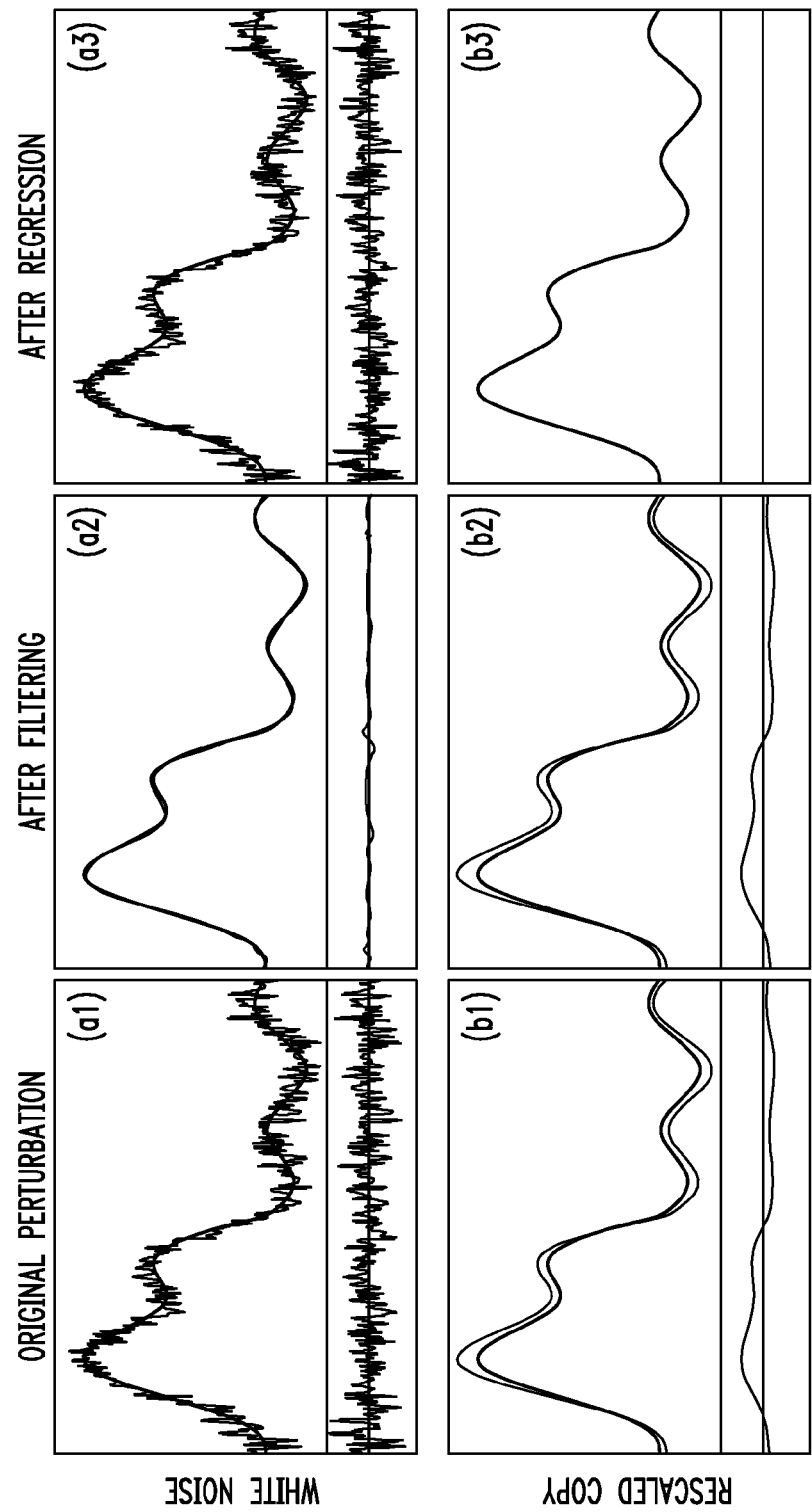
FIGS. 3a and b is a series of graphs illustrating intuition via perturbation most resilient to any true value leaks and most resilient to any linear filtering, according to an embodiment of the present invention.

The embodiments of the present invention relate to univariate time series, examine the trade-offs of methods for partial information hiding via data perturbation, and propose a practical approach that is evaluated against both filtering attacks and, also, true value leaks. Additionally, they are suited for time-evolving (i.e., non-stationary) series and can be adapted for on-the-fly data hiding in a streaming setting.

The main idea is exemplified by the two extreme cases, which are explained in more detail in below with regard to FIG. 2. True value leaks reveal the perturbation at particular time instants. If it is desired to ensure that such information does not help infer anything about the perturbation of other time instants, then necessarily each time instant must be perturbed independently of others. However, if the series exhibit certain patterns, such independent perturbation of each value in the time domain can be distinguished from the original data and filtered out. On the other hand, to ensure complete protection against any filtering method by making the perturbation completely indistinguishable from the original series, then the only way to achieve this is to make the perturbation a rescaled, exact copy of the data. However, in this case, even a single true value reveals how all other values have been perturbed.

In the first case, each time instant is perturbed independently, while in the second case all time instants are perturbed in the same way. But what if groups (or windows) of values are perturbed in the same way within a group, but differently across groups? How should these groups be chosen? Based on this insight, these questions are addressed using both Fourier and wavelet transforms.

Therefore, the embodiments of the present invention expose and study the relationship between data representation, compressibility and privacy preservation via perturbation, in the context of time series. The embodiments of the present invention also introduce the notion of compressible perturbation, which determines the best way to perturb the data depending on the perturbation magnitude and the properties of the data. Further, these embodiments examine the trade-off between breaches that exploit compressibility via filtering operations and breaches that rely on leaks of true (i.e., unperturbed) values. Finally, the embodiments of the present invention present schemes that are based on the Fourier transform and on wavelets. The wavelet-based scheme is also amenable to streaming time series.

The trade-offs between privacy and compressibility are presented, as well as the efficiency and effectiveness of the approach on real time series.

Referring initially to FIG. 1, a table provides the main notation necessary for a background on wavelets and filtering, according to an embodiment of the present invention.

Wavelets are best introduced with the Haar transform, because of its simplicity. A more rigorous introduction to wavelets along with an introduction to the Fourier transform can be found, for example, in D. B. Percival et al., "Wavelet Methods for Time Series Analysis," Cambridge Univ. Press, 2000. Given a series with N points, $v_{0,t}:=x_t$ is defined to start the Haar DWT construction. At each iteration, or level, $l=1, 2, \ldots, \log_2 N$ two operations on $v_{l-1,t}$ are performed to compute the coefficients at the next level:

Differencing, to extract the high frequencies of $v_{l-1,t}$, which gives the wavelet coefficients $w_{l,t}=2^{-1/2}(v_{l-1,2t}-v_{l-1,2t-1})$ that form the detail component of level t.

Smoothing, which averages each consecutive pair of values and extracts the remaining low frequencies of $v_{l,t}$, obtaining the scaling coefficients $v_{l,t}=2^{-1/2}(v_{l-1,2t}+v_{l-1,2t-1})$ that form the smooth component of level l.

The scaling factor of $2^{-1/2}$ ensures that the total energy (i.e., sum of squares of all values) is preserved. The coefficients of level l+1 are half as many as those of l and correspond to a time window twice the size. Construction is stopped when $w_{l,t}$ consists of one coefficient, which happens at $l=\log_2 N+1$. The total number of wavelet coefficients across levels is N-1.

There are several families' wavelet transforms that follow the above recursive pyramid algorithm, using a pair of filters, one high-pass and one low-pass. For example, in Haar wavelets, this pair consists of the simple first-order differencing and averaging filters, respectively. More generally, for each $L\geq 1$, Daubechies-L (or DB-L) wavelets use an L-th order difference filter for the high-pass operation and the corresponding low-pass filter (for more details, see, for example, D. B. Percival et al., "Wavelet Methods for Time Series Analysis," Cambridge Univ. Press, 2000). These filters have 2L non-zero coefficients.

Referring now to FIGS. 2a and b, a diagram illustrates time-frequency properties, according to an embodiment of the present invention. FIG. 2a illustrates how Haar wavelets decompose a series into time and scale. Each scale approximately corresponds to a frequency band and each wavelet coefficient within that band "summarizes" the corresponding frequency content within a localized time window. For comparison, FIG. 2b shows pure-frequency decomposition. Each coefficient contains information about a single frequency (sinusoid), but has no time information, since the basis (i.e., sinusoid) for each coefficient is not localized. In practice, series often exhibit jump discontinuities, frequency shifts or changes and other non-stationarities, therefore some localization is necessary (see, for example, D. L. Donoho, "Progress in Wavelet Analysis and WVD: A Ten Minute Tour," In Y. Meyer and S. Rogues, editors, *Progress in Wavelet Analysis and Applications*, Frontiéres, 1993). Short-window Fourier analysis uses DFT on a fixed-size window. This poses limitations on the minimum frequencies that can be captured, as well as the localization in time of each coefficient. In a wide range of application domains, the jointly varying window size and bandwidth make wavelets ideally suited for analysis and representation (see, for example, D. L. Donoho, "Progress in Wavelet Analysis and WVD: A Ten minute Tour," In Y. Meyer and S. Rogues, editors, *Progress in Wavelet Analysis and Applications, Frontiéres,* 1993; and T. Li et al., "A Survey on Wavelet Applications in Data Mining," *SIGKDD Explorations,* 4(2), 2002).

In the above example, note that estimation of both $v_{l,t}$ and $w_{l,t}$ requires only the two last scaling coefficients from the previous level, at $v_{l-1,2t}$ and $v_{l-1,2t+1}$. In general, Daubechies-L DWT requires the last 2L scaling coefficients from the previous level. Thus, it is possible to perform the DWT incrementally as new points arrive, by buffering only 2L numbers for each of the $1\leq l\leq \log_2 N$ levels. The total time required is still proportional to N, i.e., constant per new value.

Because of their time/frequency decomposition properties, wavelets have been successfully used in signal estimation and denoising (see, for example, D. L. Donoho et al., "Adapting to Unknown Smoothness Via Wavelet Shrinkage," J. Am. Stat. Soc., 90, 1995; and D. L. Donoho, "De-noising Via Soft Thresholding," *IEEE TOIT,* 41(3), 1995).

Assume that the representation of a time series with N points in some basis is given. This representation consists of N numbers and can be obtained by applying an orthonormal transform (specifically, change of coordinates) to the original series $\{x_t\}_{t=1}^N$. Also assume that the noise is i.i.d. (specifically, white) and its variance $\sigma$ is known. Given the above, the ideal denoiser is simple: any coefficient whose magnitude is below $\sigma$ is discarded as noise, otherwise it is retained. Then, the important questions are: (i) how to choose an appropriate basis, (ii) how to estimate $\sigma$ when it is not known, and (iii) what to do with the retained coefficients.

For the first question, it is ideal to want the basis that compresses the signal into the smallest possible number of coefficients or, equivalently, has the largest possible number of zero coefficients. This implies that the remaining, non-zero coefficients will have a large magnitude, making them easy to distinguish from noise coefficients. Of course, it is not possible to know this optimal representation for a single series; differently put, the optimal basis for a specific realization of a series is always just the series itself, which is not very useful. Therefore, it is desirable to choose a representation that is appropriate for a class of signals. As already mentioned, wavelets successfully compress man0y real-world series (see, for example, D. L. Donoho, "Progress in Wavelet Analysis and WVD: A Ten Minute Tour," In Y. Meyer and S. Rogues, editors, Progress in Wavelet Analysis and Applications, Frontiéres, 1993), because of their time/frequency decomposition properties and are thus an appropriate choice.

Having chosen wavelets to represent the series, it can be shown that the risk-optimal estimate of the noise variance is the median over t of the absolute magnitude, $|w_{1,t}|$, of the first-level coefficients (see, for example, D. L. Donoho et al., "Adapting to Unknown Smoothness Via Wavelet Shrinkage," J. Am. Stat. Soc., 90, 1995). Additionally, the best way to perform thresholding is to shrink each retained coefficient towards zero, rather than keeping them intact. This is also known as soft thresholding and its application to the wavelet representation is known as wavelet shrinkage.

Referring now to FIGS. 3a and b, a series of graphs illustrate intuition via perturbation most resilient to any true value leaks and most resilient to any linear filtering, according to an embodiment of the present invention. The original series consists of 200 points.

For both extremes it is assumed that, in the worst case, an attacker may have full knowledge of the true data, but in different ways. In the first, an attacker is allowed direct access to an arbitrary number of true values (in the time domain). In the second extreme, the attacker is allowed to know the shape of the series with arbitrary accuracy (specifically, the attacker may know the one-dimensional subspace spanned by the series itself). It is always assumed that an attacker uses linear functions/filters to obtain estimates of the true data (see, for example, Z. Huang et al., "Deriving Private Information from Randomized Data," In *SIGMOD,* 2005; and F. Li et al, "Hiding in the Crowd: Privacy Preservation on Evolving Streams Through Correlation Tracking," In ICDE, 2007).

FIG. 3a(1-3) illustrates the perturbation that is resilient to any number of true value leaks. In this case, each time instant must be perturbed independently of others, in order to prevent any inferences across values. This requirement is always satisfied by white noise, specifically, independent, identically distributed random values. A realization of a white noise process is shown in the bottom panel of FIG. 3(a1). This is added to the original series to obtain the published series, shown in the top panel of FIG. 3(a1). The linear regression estimate of the true values versus the perturbed values is shown in FIG. 3(a3). As expected, the true values cannot be accurately recovered. However, white noise is also uncorrelated with the original data (no matter what the data are), leading to the potential vulnerability illustrated in FIG. 3(a2), which shows the output of a wavelet-based filter.

FIG. 3b(1-3) illustrates the perturbation that is resilient to knowledge of the exact shape of the series. In this case, the perturbation must be completely indistinguishable from the original series. In other words, it should be perfectly correlated with the original series. Clearly, this is guaranteed if the perturbation is an exact copy of the original series, except for rescaling of all values by the same factor. The result is shown in FIG. 3(b1), with the same perturbation magnitude as in the previous example. As expected, any kind of linear filtering is unable to separate the perturbation from the true series—FIG. 3(b2). However, if even a single true value is leaked, then evidently all true values can be inferred, as illustrated in FIG. 3(b3), which shows the linear regression estimates.

Figure 4:
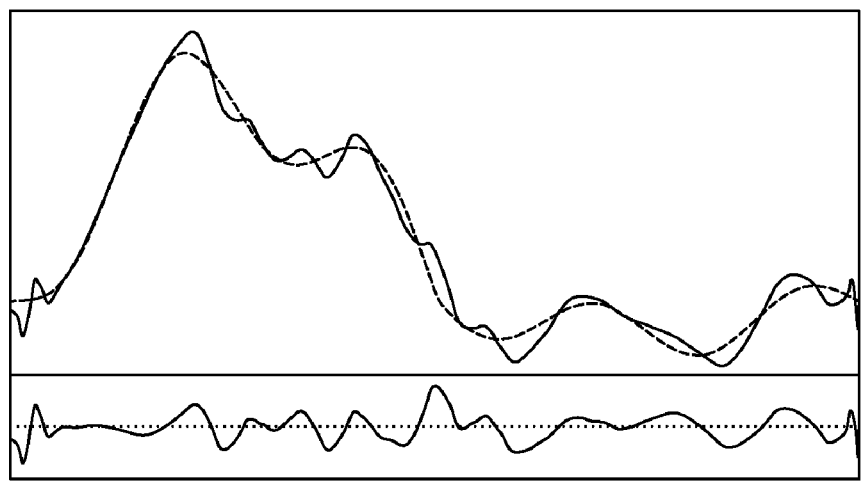
FIG. 4 is a graph illustrating a perturbation with the same smoothness properties as the data under a broad linear class of series that prevents linear reconstruction based on true value leaks according to an embodiment of the present invention.

Referring now to FIG. 4, a graph illustrates a perturbation with the same smoothness properties as the data under a broad linear class of series that prevents linear reconstruction based on true value leaks according to an embodiment of the present invention.

Figure 5:
FIG. 5 is a diagram illustrating a summary of the two extreme assumptions about background knowledge, and the corresponding best choices for perturbation, according to an embodiment of the present invention.

Referring now to FIG. 5, a diagram illustrates a summary of the two extreme assumptions about background knowledge, and the corresponding best choices for perturbation, according to an embodiment of the present invention. An adversary may have a combination of background knowledge, therefore it is desirable to automatically find a balance between fully deterministic and fully independent perturbation. In FIG. 4, neither filtering nor linear estimation based on leaks can remove more than 1% of the perturbation. Practical techniques are proposed to address this challenge and evaluate them on a number of real datasets.

A common measure of uncertainty is standard deviation, specifically, root mean square value of a series. Standard deviation is used to measure two important aspects: (i) discord between perturbed and original data, and (ii) remaining uncertainty about the true values, after attempts to recover them. It is desirable for the discord to be as low as possible and, in particular, at most equal to a chosen threshold. The utility of the published data drops as the discord increases (see, for example, A. Evfimievski et al., "Limiting Privacy Breaches in Privacy Preserving Data Mining," In PODS, 2003; and D. Kifer et al., "Injecting Utility into Anonymized Datasets," In SIGMOD, 2006). On the other hand, given the discord, it is desirable for the remaining "true" uncertainty to be as high as possible, ideally equal to the discord. These notions are formally defined below.

Additive Perturbation—Given a series $x_t$, for $t \geq 1$, a corresponding perturbation series $n_t$ is chosen with zero mean, $E[n_t]=0$, and publish the series $y_t := x_t + n_t$, for all $t \geq 1$.

Discord—Discord $\sigma$ is the standard deviation of the perturbation, i.e., $$\sigma^2 := \text{Var}[y_t - x_t] = \text{Var}[n_t] = E[n_t^2].$$

The discord threshold is given and determines both the maximal loss of information that is tolerable, as well as the maximum uncertainty that can be introduced. In fact, these two quantities should be equal and this is precisely the goal. However, they may not be equal, because an adversary can apply techniques that reduce the uncertainty.

Given the discord threshold, the available perturbation latitude is always fully exploited, specifically, the goal will be to add a perturbation amount equal to the threshold. Thus, from now on, the discord and its threshold are not distinguished, using $\sigma$ to denote both.

Given the published values $y_t$, for $t \geq 1$, an adversary may attempt to obtain an estimate of the true values, which may reduce the overall uncertainty. The discord (specifically, uncertainty originally introduced by the data publisher) is the standard deviation of the difference between true and published values. Similar to this, the remaining uncertainty is measured with the standard deviation of the difference between true values and the adversary's estimates. This remaining uncertainty is a measure of privacy achieved under each attack setting.

Two attempts are considered for estimating the true values, each with different, worst-case assumptions about the background knowledge available. In both cases, it is assumed that an adversary applies linear functions or filters to obtain an estimate of the true values.

The fast one relies on linear filtering methods, which attempt to separate the perturbation from the true data. The filtering technique employed is described above and has been proven very successful in a wide range of domains and applications (see, for example, D. L. Donoho et al., "Adapting to Unknown Smoothness Via Wavelet Shrinkage," J. Am. Stat. Soc., 90, 1995; and D. L. Donoho, "De-Noising Via Soft Thresholding," IEEE TOIT, 41(3), 1995).

Filtering Uncertainty—Let $\tilde{y}_t$ be the result of a linear filtering operation on the published series $y_t$. The filtering uncertainty is the remaining uncertainty after this operation, i.e., $$\tilde{\sigma}^2 := \text{Var}[\tilde{y}_t - x_t].$$

In practice, the standard deviation $\tilde{\sigma}$ of the filter's output is estimated by applying the filtering operation on a finite time series consisting of N points and using the sample estimate of the standard deviation, $$\tilde{s}^2 := \sum_{t=1}^{N} (\tilde{y}_t - x_t)^2 / N.$$

With a slight abuse of notation, the sample estimate is also denoted with $\tilde{\sigma}$ instead of $\tilde{s}$.

In this case, an adversary has the background knowledge that the signal has a compact representation in some space, and more specifically, that the largest fraction of its energy is concentrated on a few transform coefficients. This is a very common assumption in signal estimation and recovery (see, for example, D. L. Donoho, "Compressed Sensing," *IEEE TOIT*, 52(4), 2006; and D. L. Donoho, "De-Noising Via Soft Thresholding," *IEEE TOIT*, 41(3), 1995), and amounts to a constraint on the "shapes" that the series is allowed to have. All practical applications of signal recovery need to make an assumption about the actual transform. Wavelet-based techniques have been shown most successful for a wide range of real-world signals (see, for example, D. L. Donoho et al., "Adapting to Unknown Smoothness Via Wavelet Shrinkage," J. Am. Stat. Soc., 90, 1995), performing at least as well as Fourier-based techniques.

The second kind of attempt to partially remove the perturbation relies on true value leaks. By construction $y_t = x_t + n_t$, and, if $n_t$ is Gaussian white noise, this is precisely the model for least-squares linear regression. This observation leads naturally to the next definition.

Leak Uncertainty—Let $\hat{y}_t$ be the linear regression estimate obtained by fitting a line to the true vs. perturbed values, i.e., $\hat{y}_t = \alpha y_t + \beta$ where $\hat{y}_t$ are chosen so as to minimize the residual error $\Sigma_t(x_t - \tilde{y}_t)^2$. This RMS error is the measure of true value leak uncertainty, i.e., $$\tilde{\sigma}^2 := \text{Var}[\tilde{y}_t - x_t].$$

In practice, it is desirable to estimate $\tilde{\sigma}$ from a finite sample. The least-squares estimators of $\alpha$ and $\beta$ are $$a := \frac{\sum_{t=1}^{N}(x_t - m_x)(y_t - m_y)}{\sum_{t=1}^{N}(x_t - m_x)^2}, \text{ and } b := m_y - a m_n$$

where $m_x = \sum_{t=1}^{N} x_t/N$ and $m_y = \sum_{t=1}^{N} y_t/N$ are the sample means. The sample estimate of the residual variance is $$\hat{s}^2 := \sum_{t=1}^{N}(x_t - a y_t - b)^2.$$

Since a and b are unbiased estimators, their expectation over all finite samples is $E|a| = \alpha$ and $E|b| = \beta$.

Leak uncertainty is the minimum error that can be achieved by any linear function for estimating the true values, even if it is assumed that an adversary knows all true values. Therefore, the measure is a worst-case estimate of privacy loss, under the assumptions that an adversary uses linear estimation techniques and has access to any number of true values.

Furthermore, the distribution of $N\hat{s}^2/\tilde{\sigma}^2$ is $\chi^2$ with N−2 degrees of freedom (see, for example, M. H. DeGroot et al., "Probability and Statistics," Addison Wesley, 3rd ed. edition, 2002). Therefore, even if a small subset of M<N samples was used to estimate $\hat{s}$, its expectation over all leaks of size M would still be $E[\hat{s}^2] = \tilde{\sigma}^2(M-2)/M \approx \tilde{\sigma}^2$. The standard deviation Dev[$\hat{s}^2$] drops quickly, in proportion to $\tilde{\sigma}^2/M$. Finally, again with a slight abuse of notation, from now on $\tilde{\sigma}^2$ will be used instead of $\hat{s}$.

For single time series, trends and patterns often refer to bursts (see, for example, Y. Zhu et al., "Efficient Elastic Burst Detection in Data Streams," In *KDD*, 2002) and dominant periods (see, for example, M. Vlachos et al., "Structural Periodic Measures for Time-Series Data," DMKD, 12(1), 2006). Such analysis is largely performed on the spectrum of the signal. Whether a perturbation preserves these key properties depends on (i) how much perturbation is added, which is the discord, and (ii) how the perturbation is added. In most perturbation methods, the first is a parameter determined by the end user. Additionally, both of perturbation techniques, naturally preserver the spectral and "smoothness" properties of the original signal, by design. Hence, the proposed perturbation techniques will be useful in preserving both privacy and utility of time series.

Two potential breaches are considered with different assumptions about background knowledge. In the first case, it is assumed that an adversary knows that a series has a compact representation in some linear subspace (for example, few non-zero wavelet or Fourier coefficients). In the second case it is assumed that an adversary knows any number of true values, in the time domain. In both cases it is assumed that linear estimation techniques are used. Practical techniques are proposed to address both challenges and the techniques are evaluated under the two different attack models on a number of real datasets.

As pointed out, the simple solution of perturbing the series with white noise does not work, because white noise is incompressible under any representation (or basis). As a result, the added perturbation is "diluted" over coefficients that are not important in representing the series. Consequently, a large portion of the white noise can be removed, leading to a significant decrease in remaining, true uncertainty over individual true values. Thus, the goal is to avoid this problem, by appropriately adapting the perturbation to the original series.

The perturbation $n_t$ for each value at time t will be chosen based on a given discord a and, of course, the series $\{x_t\}$ itself. Since (i) it is impossible to design a method that is optimally resilient against both filtering and leak attacks, and (ii) filtering is possible at any and all time instants since it requires no prior knowledge about the true data, resilience is used for filtering as the primary guide in designing the techniques, but also taking leak attacks into consideration and the methods are evaluated with respect to both potential attacks. The general steps to construct the perturbation are:

(S0) Choose a "description" or basis.
(S1) Perturb only those coefficients that are "important" (to be made precise later) in the chosen description.
(S2) Determine by how much to perturb them.

The first step consists of applying an orthonormal transform which, given the N time domain values $x_t$, for $1 \leq t \leq N$, will produce another set of N coefficients, $c_i$ for $1 \leq i \leq N$. Next, it is assumed for the moment that Gaussian white noise is added with variance $\sigma^2$. This simply means that each coefficient is perturbed by a random number c, drawn according to a Gaussian distribution with zero mean and standard deviation $\sigma$, $c_i \leftarrow \text{GaussRandom}(0, \sigma)$ for all $1 \leq i \leq N$. This may be thought of as allocating N noise "units" (each corresponding to a per time instant perturbation of magnitude $\sigma$) equally into all N coefficients. Note that the resulting perturbation sequence $n_t$ for $1 \leq t \leq N$ has the same statistical properties (specifically, Gaussian white noise with the same variance) under any orthonormal basis. Therefore, for i.i.d. Gaussian $n_t$, the choice of representation is not important.

However, it has been established that this approach is susceptible to filtering attacks. Therefore, a basis is chosen that successfully compresses a large class of time series, in the sense that it concentrates its energy into a few transform coefficients. Recall that the ideal denoiser, given a basis, discards all coefficients below the (true or estimated) noise variance. Therefore, any noise embedded into such coefficients is "wasted," as it can be easily separated from the dominant coefficients. This observation leads to the conclusion that only those coefficients with magnitude greater than $\sigma$ are "important" for perturbing the data in a way that is resilient to filtering attacks.

Therefore, instead of allocating the N available noise units into all N coefficients, they are allocated to the set of coefficients whose magnitude exceeds $\sigma$. Let $I:=\{i:|c_i|\geq\sigma\}$ be the set of their indices. However, in order to ensure that $\text{Var}[n_t]=\sigma^2$, the variance of the random number that will be added to each $c_i$, for $i\in I$ needs to change as well. For example, a simple choice would be a random number with variance $\rho_i:=N/K$ to each of them, where $K:=|I|$ is the number of coefficients that exceed $\sigma$. This ensures that $E[\Sigma_i c_i'^2/N]=E[\Sigma\Sigma_{i\in I}c_i^{2'}]/N+E[\Sigma_{i\notin I}c_i^2]/N=K\sigma_i^2\sigma^2/N+(N-K)\cdot 0/N=K(N/K)\sigma^2/N+0=\sigma^2$, since each $c_i\in C$ is perturbed independently. In other words, the expected sample variance of the perturbation series will be $\sigma^2$ as desired. More generally, any $\rho_i$ is chosen such that $\Sigma_i \rho_i^2=N$.

Referring now to FIG. 6, a chart illustrates the general steps (S0-2) for compressible perturbation, according to an embodiment of the present invention. These steps are described in more detail below.

In this section, two batch perturbation methods are proposed that rely on pure frequency or time/frequency representations of the series. In particular, the first is based on the well-established Fourier representation of the entire, length-N series. The second is based on the wavelet representation. First, Fourier and wavelet perturbation are studied in a batch setting and the wavelet-based scheme is revisited, adapting it to a streaming setting.

Referring now to FIG. 7, a chart illustrates the steps for pure frequency perturbation or compressible perturbation, using the Fourier representation, which decomposes the series into pure sinusoids, according to an embodiment of the present invention. $\chi_k$, $1\leq k\leq N$ is denoted with the Fourier transform of $x_t$, and with $v_k$ the Fourier transform of the perturbation $n_t$ that is desirable to construct. For simplicity, the pseudocode only shows the case for N odd. If N is even, then the Fourier coefficient $\chi_{N/2+1}$ at the Nyquist frequency must be treated as a special case.

Intuitively, each sinusoid is perturbed by randomly changing its magnitude and phase (lines 4-5 in FIG. 7). In more detail, since $x_t$ is real-valued, its Fourier transform is symmetric, i.e., $$\chi_{k+1}=\chi^*_{N-k+1},\text{ for }k=\begin{cases}1,\ldots,(N-1)/2 & \text{if }N\text{ odd}\\ 1,\ldots,N/2-1 & \text{if }N\text{ even}\end{cases},$$

where $\chi_{N-k+1}^*$ denotes the complex conjugate of $\chi_{N-k+1}$. The DC coefficient $\chi_1$ is always real and equal to the series mean. If N is odd, then $\chi_{N/2+1}$ is also real (case not shown in FIG. 7). It is ensured that $v_k$, $1\leq k\leq N$, also satisfies the same property (line 5 in FIG. 7), so that the perturbation is also real-valued.

Because of Equation (1), essentially the first half of the Fourier transform carries all the necessary information. The per-frequency energy (or, more accurately, its square root) is computed in line 1 of FIG. 7 from Equation (1), $|\chi_{k+1}|=|\chi_{n-k+1}|$, so that $\Sigma_k p_k^2=\Sigma_t x_t^2$ (assuming that $x_t$ is zero mean). This information is then used to decide which frequencies to perturb.

Referring now to FIG. 8, a graph illustrates lines 4-5 of FIG. 7, according to an embodiment of the present invention. For each frequency that exceeds $\sigma$, a complex Gaussian random number is chosen, which perturbs the amplitude and phase independently.

The allocation of "noise units" into the important frequencies is done in proportion to N/K as well as in proportion to the energy content of each perturbed frequency (factor of $p_k^2/P$ in line 3 of FIG. 7). This is the best choice for resilience to filtering attacks, as it tends to concentrate most of the perturbation into a few dominant frequencies. However, this may increase the "regularity" of the perturbation and make it somewhat more susceptible to true value leaks. Per-band weighting of the frequencies above the threshold $\sigma$ (specifically, inclusion of the $p_k/P$ factor in $\rho_k$, line 3 of FIG. 7) has small impact on true value leaks, while in certain cases significantly reduces resilience to filtering attacks. As further described below, the wavelet representation does not suffer from such problems, allowing a simpler decision on how to allocate "noise units".

Fourier-based perturbation generally performs well for series that are dominated by a few frequencies which do not change over time. If the series has discontinuities or frequency shifts, then Fourier may perform worse, because phenomena localized in time are spread across frequencies. This effect would allow a potential attacker to remove more uncertainty, roughly in proportion to the magnitude of such discontinuities (either in time or in frequency) and in inverse proportion to the number of frequencies.

Finally and more importantly, the Fourier transform of a growing series cannot be updated incrementally. One potential solution might be to use the short-time Fourier transform (STFT), but a fixed-size time window is undesirable. Next, a wavelet-based perturbation method is developed. Wavelets employ multiple window sizes to decompose the series and are also amenable to streaming estimation.

Referring now to FIG. 9, a chart illustrates the steps of Time/frequency compressible perturbation using the wavelet transform, according to an embodiment of the present invention. $w_{l,t}$ and $\omega_{l,t}'$ are denoted as the wavelet coefficients of the data $x_t$ and the perturbation $n_t$, respectively. FIG. 9 follows the same general design of FIG. 5. In fact, wavelet coefficients are always real numbers and the procedure is simpler and more intuitive than FIG. 7. "Noise units" are allocated only to those coefficients that exceed $\sigma$ in absolute value. The perturbation is allocated equally among them, specifically, only in proportion to N/K (without weights in proportion to per-coefficient or per-level energy). This simple choice makes the perturbation more resilient to true value leaks, but without sacrificing resilience to filtering attacks in practice, unlike FIG. 7. The reason is that time-localized phenomena do not lead to smearing of energy across coefficients.

Wavelets have been successful in a wide range of settings (see, for example, T. Li et al., "A Survey on Wavelet Applications in Data Mining," SIGKDD Explorations, 4(2), 2002) and are more resilient to changes in series' characteristics. They decompose the series into translated and dilated, localized waves at multiple scales, which correspond to a particular time and frequency window. Short windows are employed for high frequencies (specifically, short periods) and longer windows for lower frequencies (specifically, longer periods).

The localization of bases in time has the additional desirable characteristic that, intuitively, each period is perturbed independently of others. For example, assume that by following an automobile, its true speed is learned over a period of 15 minutes. However, if periodic trends shorter than 15 minutes are perturbed independently, collected true values can tell nothing about the future perturbation at scales of up to 15 minutes. For periodic trends in the next scale of 30 minutes, perhaps the information learned will be useful for another 15 minutes, but not longer, and so on for scales of 60 minutes, etc.

Finally, the DWT can be computed in O(N) time, as opposed to O(N log N) time required by FFT (see, for example, D. B. Percival et al., "Wavelet Methods for Time Series Analysis," Cambridge Univ. Press, 2000). Thus, even in a batch setting they are computationally more efficient. Furthermore, wavelets can be estimated incrementally, using just O(log N) total space and O(1) amortized time per value. Since they have several desirable benefits, wavelets are focused on.

It is a goal to choose an effective perturbation that is hard to remove, but it is desirable to perturb values as they arrive, before seeing the entire series, which grows indefinitely. Furthermore, it is desirable to minimize or eliminate publishing delay.

The Fourier transform needs, by definition, the entire series which is clearly not possible in this case. One solution is to partition the series into fixed-size windows and apply Fourier on each of them. However, if a small window is used, it is not possible to capture trends with period larger then the window length. For example, if a 5-minute window is used to perturb driving speed, it is still possible to leverage hourly or daily driving patterns to reduce uncertainty. If a large window is used, then it may be necessary to delay publishing the data until the window is filled up, so it is analyzed and perturbed. Alternatively, the frequencies could be used from the previous window to perturb the current one. However, if the window is large, it may not capture trends that have substantially changed in the new window. For example, a car might have been on the highway driving with a constant speed during the last hour, but has now entered a city and is in stop-and-go traffic. If a single one-hour window is used, the perturbation will follow the wrong trends.

Thus, the time/frequency decomposition of wavelets, which use multiple windows proportional to the period is desirable. In this case, the information of the last, for example, 5 minutes, is used to decide if and how to perturb, during the next 5 minutes, patterns up to that long. However, the information of the last 10 minutes is used to make the same decision for smoother, longer patterns (up to 10 minutes) during the next 10 minutes, and so on. However, steps (S1-2) of FIG. 6 need to be re-examined in a streaming context.

Revisiting step (S1). If it is desirable to make an exact decision whether to perturb a coefficient $w_{l,t}$ based on its actual magnitude (lines 2 and 3-4 in FIG. 9), then a wait time proportional to $2^l$ for coefficients at level l is necessary. In order to perform the inverse wavelet transform to publish a value, all coefficients across all levels that may affect its value must be waited for. However, since the series size N grows indefinitely, so does the number of levels L=O(log N), which implies an indefinite publication delay.

A maximum delay (equivalently, a maximum level willing to wait for) may be imposed, but that is effectively the same as using a fixed-length window. Instead, the noise is embedded into the next coefficient of the same level, specifically, $\omega_{l,t+1}'$ is used instead of $\omega_{l,t}'$ in lines 3 and 4. Said differently, the important coefficients in step (S1) are chosen based on the magnitude of previous coefficient at same band. For example, referring now to FIG. 10, a diagram illustrates the order of incremental estimation, according to an embodiment of the present invention. The first coefficients of each level (darker shade) won't be perturbed, whereas the decision on whether to perturb the lightly shaded coefficients will be based upon the previous (darker) coefficient on the same level.

This simple one-step prediction is effective, since the only interest is whether a coefficient exceeds σ, rather than in its exact value. More specifically, periodic trends result in uniformly large coefficients at the corresponding wavelet level. Bursts also tend to affect more than one consecutive coefficient—if not, that is the only case that may be missed. However, such very short bursts generally occur at small scales and can safely be ignored.

Revisiting step (S2). The number K of coefficients exceeding σ (line 1 of FIG. 9) is not available at the time needed to make a decision about how to perturb the data. This quantity is needed to determine ρ:=N/K. The approach is to substitute these with incremental estimates. Therefore, whenever a new wavelet coefficient $\omega_{l,t}'$ for any l and t is produced, the estimate of ρ is updated as follows:

N←N+1 if $|w_{l,t}| \geq \sigma$ then

K←K+1

ρ←λρ+(1−λ)(N/K)

Figures 10, 11:
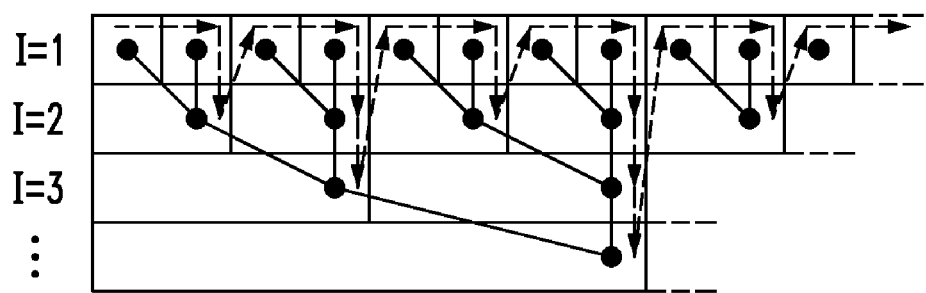
FIG. 10 is a diagram illustrating the order of incremental estimation, according to an embodiment of the present invention.
FIG. 11 is a summary of the datasets, which range from environmental monitoring to financial data, with a wide variety of characteristics, according to an embodiment of the present invention.

The order in which wavelet coefficients are incrementally computed is shown in FIG. 10. This is the order in which the running counters N and K are updated. The decay factor λ=0.9 is meant to prevent wild fluctuations, particularly in the beginning of the series when both N and K are relatively small. The inverse wavelet transform can be performed incrementally in a similar fashion.

The inverse DWT can be computed incrementally in O(1) time per value, using O(log N) space. The forward transform can be performed incrementally because it is a post-order traversal of the coefficient tree (see FIG. 10). The inverse transform is a preorder traversal of the same tree.

The methods of the present invention are evaluated on several series from the UCR Time Series Data Mining Archive (TSDMA) (see, for example, E. Keogh et al., "Ucr Time Series Data Mining Archive," http://www.cs.ucr.edu/~eamonn/TSDMA/)—see FIG. 11 for a summary of the datasets, which range from environmental monitoring to financial data, with a wide variety of characteristics. All datasets are normalized to unit variance to standardize comparisons. The length of Light and Chlorine is 2048 and of SP500 it is 16384—the choice of powers of two is without loss of generality, to simplify implementation. In more detail, Chlorine is collected using a EPANET 2.0 that accurately simulates the hydraulic and chemical phenomena within drinking water distribution systems, given a realistic description of the network, demand patterns, pressures and flows at each node. The time series represents the chlorine concentration level at one junction in the network. The content of these measurements is concentrated on a few frequencies, that do not change over time, and the remaining frequencies have almost zero content across time (i.e., below σ). The Light dataset consists of light intensity measurements collected using a Berkeley Mote at a particular location in a lab. These measurements exhibit strong daily periodic trends, however, the trends' shape is non-sinusoidal, with many sharp edges and discontinuities. The SP500 dataset contains the daily values of the Standards & Poors 500 stock market index, over a period of approximately 60 years. Even though the frequency content over such a long period is concentrated on few frequencies, there several above σ.

The prototype is built in Matlab 7, running on a Pentium M 2 GHz with 2 GB memory. The Wavelet Toolbox is used for batch wavelet transforms, as well as for wavelet denoising (SureShrink [see, for example, D. L. Donoho et al., "Adapting to Unknown Smoothness via Wavelet Shrinkage," *J. Am. Stat. Soc.*, 90, 1995], with DB-4 wavelets and the rigorous version of single-level noise estimation). One experimental run is performed for several different values of the discord σ, ranging from 5% to 40% of the total series standard deviation, at steps of 5%. For each experiment and for each method, ten perturbation trials are run. Each trial produces a different random perturbation. The baseline method is white noise (i.i.d. Gaussian random perturbation) and included are (i) batch wavelet perturbation (DWT), (ii) its streaming version (Streaming DWT), and (iii) Fourier perturbation (FFT, comparing two noise allocation schemes—all figures are with per-band weighting as in FIG. 7, line 3, unless otherwise noted).

It is first examined how much uncertainty can be removed by either a filtering or a true value leak attack on data perturbed with each method. In particular, the fraction of uncertainty removed is examined, i.e., $$\tilde{f}(\sigma):=(\sigma-\tilde{\sigma})/\sigma \text{ and } \hat{f}(\sigma):=(\sigma-\hat{\sigma})/\sigma,$$

for several different values of the discord a (ranging from 5% to 40%). Both the maximum (specifically, worst-case value) and average of $\tilde{f}$ and $\hat{f}$ are estimated across the ten perturbation trials in each experiment.

Figure 12:
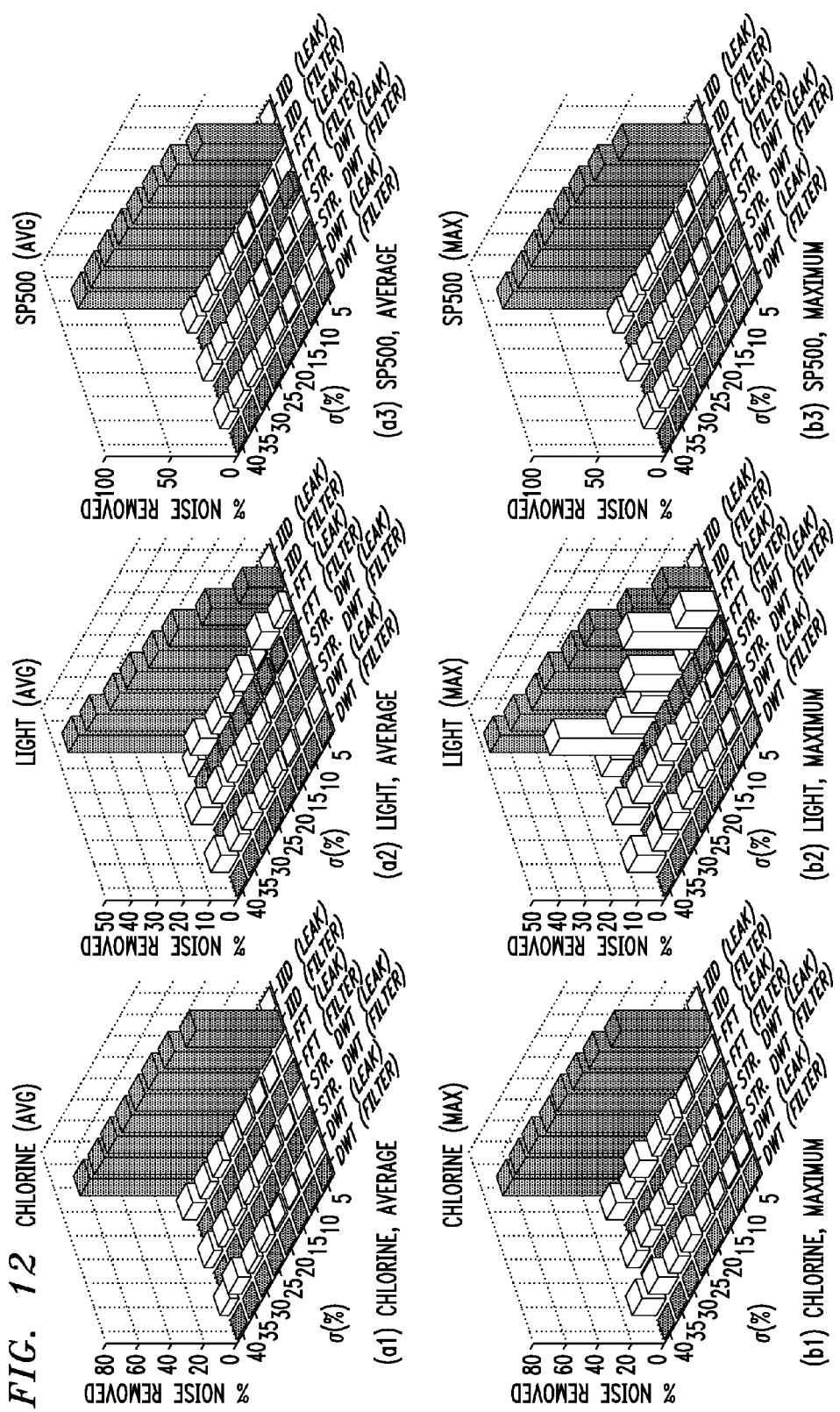
FIG. 12 is a series of diagrams illustrating the percent of noise removed by filtering, for each of the methods, according to an embodiment of the present invention.

Referring now to FIG. 12, a series of diagrams illustrate the percent of noise removed by filtering, for each of the methods: (i) filtering and leak attack reduction for batch wavelet method (first two bars from left, dark blue and blue); (ii) filtering and leak reduction for streaming wavelet method (next two bars, light blue and cyan); (iii) filtering and leak reduction for Fourier method (always batch, next two bars, light green and orange); and (iv) filtering and leak reduction for white noise (last two bars to the right, red and brown), according to an embodiment of the present invention.

Note that, by construction, reconstruction from true value leaks does not help at all for white noise (even though not visible, all bars are zero). However, filtering can very successfully remove from 20-30% of the perturbation (for Light) up to almost 90% (for SP500). Thus, the need to take into account the characteristics of the series by using an appropriate, concise description is clear beyond doubt.

Having established this, it is observed that all three of the proposed methods perform similarly. The streaming, wavelet perturbation method performs slightly better than the other two in some occasions. The reason is that it may initially overestimate the "density" $\rho=N/K$, particularly for series that have a large number of coefficients below the discord $\sigma$. This results in adding slightly more noise which, however, is never beyond 1-3% more than desired. Fourier perturbation may perform somewhat worse on certain data. However, as described below, it may exhibit sensitivity to certain data characteristics and, in particular, the presence of sharp discontinuities. Overall, however, all three methods perform well on a wide variety of series and stay close to the optimal diagonal.

Finally, for wavelet-based perturbation, the average and maximum uncertainty reduction are closer to each other. In some cases the discrepancy between the two is larger for Fourier. Thus, even though all three methods have similar average behavior, wavelets perform more consistently.

In order to measure the uncertainty $u(\sigma)$ that remains after attempted attacks of any type, the fraction of the perturbation that remains in the worst case (i.e., after the most successful of the two attacks) is also shown. In particular, $$u(\sigma):=\min\{\sigma(1-\tilde{f}(\sigma)),\sigma(1-\hat{f}(\sigma))\},$$

where $\tilde{f}(\sigma)$ and $\hat{f}(\sigma)$ are estimated over ten trials, as explained before.

Figure 13:
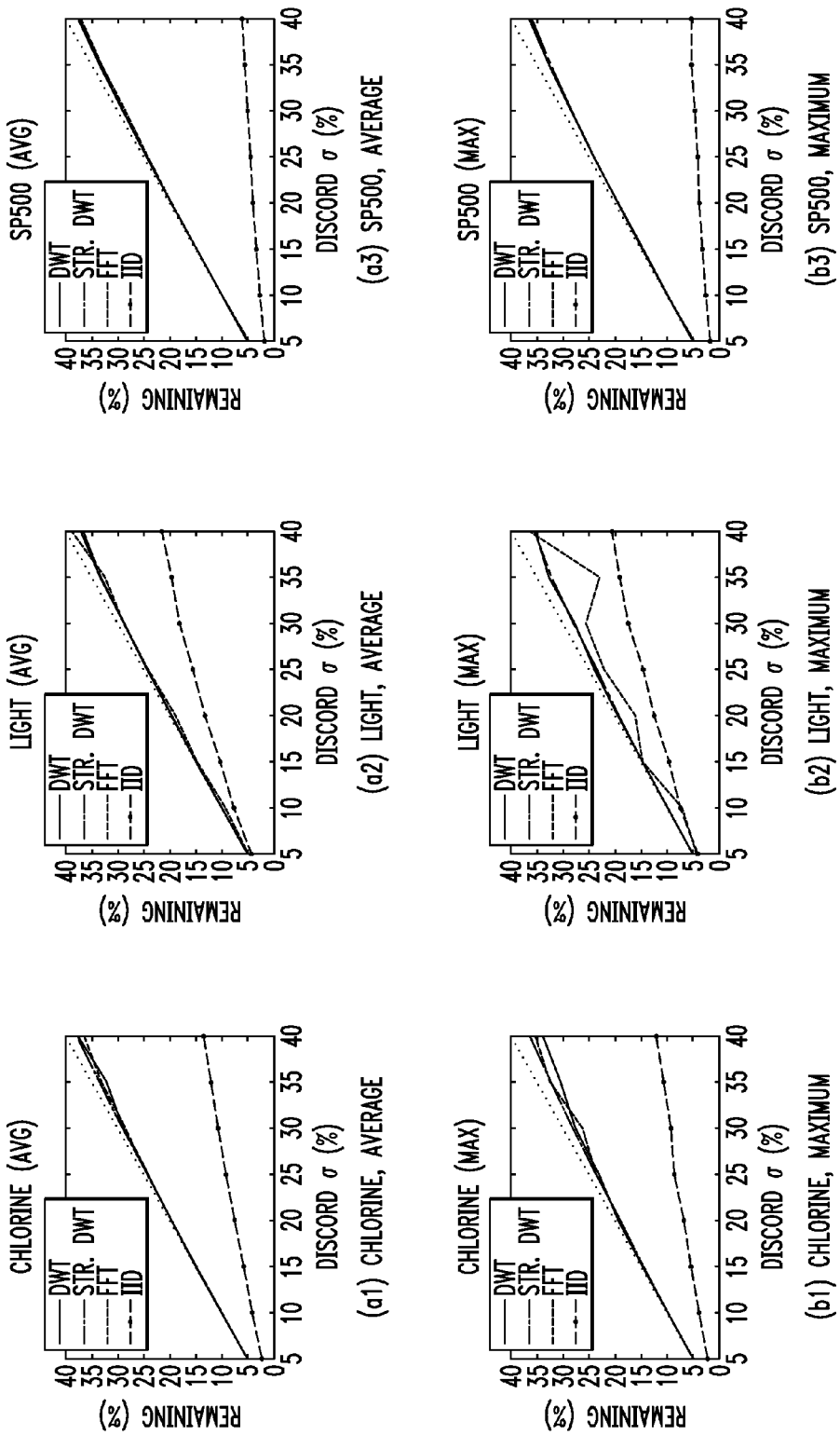
FIG. 13 is a series of diagrams illustrating the remaining uncertainty for all different methods, according to an embodiment of the present invention.

Referring now to FIG. 13, a series of diagrams illustrate the remaining uncertainty for all different methods, according to an embodiment of the present invention. The axis diagonal, which represents the ideal case (specifically, remaining uncertainty equal to the discord) is plotted with a light gray, dashed line. The closer a method lies to this line, the better its overall performance.

First, it is clear in these plots as well that white noise performs very poorly, allowing a very large reduction of uncertainty. All three of the proposed methods perform similarly. In Light, which exhibits sharp discontinuities, the largest fraction of the energy concentrated on daily and half-daily periods. Most of the remaining energy is smeared across frequencies, due to the frequent jumps. Thus, this concentration of energy on a few frequencies allows somewhat larger uncertainty reduction via leaks, due to the regularity of the perturbation.

Noise allocation in proportion to frequency band energy, and is compared to equal allocation. The comparison is performed for both Fourier and wavelet perturbation. By default, FIG. 7 as presented uses per-band allocation. Changing line 3 to $\rho_k \leftarrow N/K$ and ignoring the $p_k/P$ factor is the modification necessary to do equal allocation. On the other hand, the default for FIG. 9 is equal allocation. To change it into per-brand allocation, the level energy, $p_l \Sigma_{t \in I_l} w_{l,t}^2$, and the total energy, $P \leftarrow \Sigma_l p_l$ is first estimated. From these $\rho_l \leftarrow (p_l/P) \cdot (N/K)$ is estimated and then $\rho_l$ is used instead of $\rho$ in line 3 of FIG. 9.

Referring now to FIG. 14, a diagram illustrates noise allocation for light, according to an embodiment of the present invention. Referring also to FIG. 15, a series of diagrams illustrate per-band weighting versus equal allocation for noise allocation, according to and embodiment of the present invention. FIGS. 13 and 14 show the comparison of allocation schemes on the two most representative datasets. The evaluation justifies the default allocation schemes for each algorithm and shows they are in line with the design principle: make the simplest choice that is resilient to filtering attacks, while also keeping true value leak attacks in check.

On Chlorine, which consists mainly of a few, unchanging frequencies, Fourier perturbation performs similarly under both allocation schemes—see FIG. 15(a1-2). However, Light has a dominant daily trend but also a large number of discontinuities that are smeared across frequencies. Thus, with equal allocation, Fourier "wastes" too much noise units on those frequencies and this can be effectively detected and removed by filtering—see FIG. 15(b2). With per-frequency allocation, Fourier performs acceptably, on average. However, its performance is less stable than the wavelet perturbation, as is evident in FIG. 12(b2) which shows worst-case measurements. Overall, wavelets perform at least as well as Fourier, in a more consistent fashion due to their time-localization properties.

Figure 16:
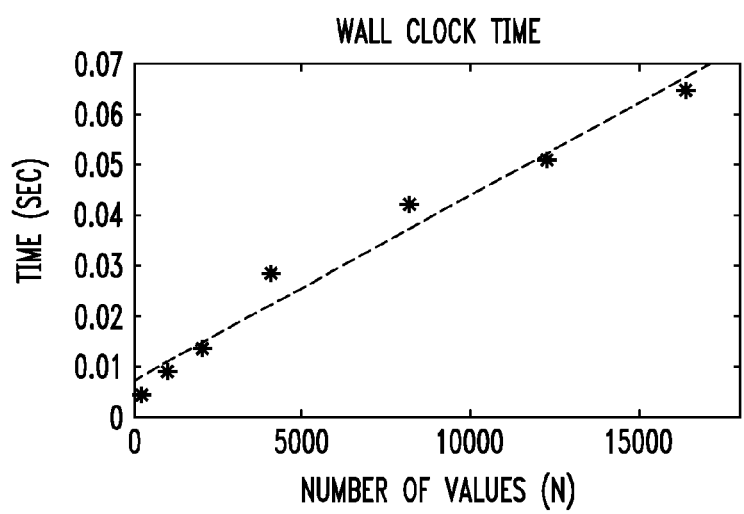
FIG. 16 is a diagram illustrating scalability with respect to number of values, according to an embodiment of the present invention.

Referring now to FIG. 16, a diagram illustrates scalability with respect to number of values, according to an embodiment of the present invention. FIG. 16 verifies that the wavelet perturbation scheme scales linearly with respect to time series stream size. Even though the prototype is implemented in Matlab, the average processing time per value is approximately 35 μsec, when the stream size is large enough to compensate for initial overheads.

The experimental evaluation clearly shows that white noise is insufficient for effective perturbation, particularly under the filtering attacks which are the primary concern. Thus, it is necessary to take the structure of the data into consideration, by seeking an effective, concise description of real data. Three methods are proposed which perform similarly on average. For series with stable spectral content limited to a small number of frequencies, all methods perform similarly. If the spectral content changes, then Fourier performs well on average but is less consistent overall. The perturbation method of the present invention that uses time/frequency wavelet analysis performs as well as or better than Fourier and is also suitable for streaming estimation.

Two potential breaches are considered, with different assumptions about background knowledge, each of which captures situations that may arise in practice. In particular, the first set of assumptions is most common in signal estimation and recovery applications, and essentially imposes either "global smoothness" constraints (via the background assumption of compact representation in the frequency domain) or "local smoothness" constraints (via the assumption of compact representation in the wavelet domain). The second set of assumptions deals with true value leaks and efforts for linear estimation of other true values, based on those that were leaked. In this case the worst-case view is taken that an arbitrary number of true values may be leaked. The leak uncertainty is a statistical measure of the maximum possible loss of privacy under these assumptions.

The embodiments of the present invention focus on practical aspects and the methods are extensively evaluated under both attack models, demonstrating that both are important in practice. In addition, the experimental evaluation presents both average-case results, in FIG. 12($a$1-3) and FIG. 13($a$1-3), as well as worst-case results, in FIG. 11($b$1-3) and FIG. 13($b$1-3). Average-case results are important to judge the overall behavior of a technique, but worst-case results are also important, since they more accurately reflect what may happen on a particular publication instance of one dataset. Perhaps because of the challenges in proving meaningful statements in the latter case, worst-case analysis has been overlooked. The evaluation demonstrates the practical robustness of the techniques on a number of datasets.

In general, filtering attacks based on background knowledge about the "smoothness" properties of the data are the most important in practice. This is clear in all cases of FIG. 12, where between 50-90% of an i.i.d. perturbation may be removed. Among the two classes of smoothness assumptions an adversary may make (global, via Fourier, or localized at multiple scales, via wavelets), wavelet-based techniques perform at least as well as Fourier-based techniques. Only for Chlorine with smaller perturbation magnitudes, the Fourier-based technique performs slightly better. However, Fourier-based global analysis is not suitable for streaming publication of the data. Furthermore, for datasets with both strong periodic components as well as local discontinuities, such as Light, Fourier-based perturbation tends to concentrate on a few frequencies, resulting in regularities that may be exploited by true value leaks, as illustrated in FIG. 12($b$2).

In summary, two novel aspects of partial information hiding and privacy are focused upon. Two real-world scenarios are considered; design robust and practical techniques which are also suitable for a streaming setting. For each aspect, the techniques of the present invention are evaluated extensively on real data.

From the first, seminal work on privacy preservation via partial data hiding (see, for example, R. Agrawal et al., "Privacy Preserving Data Mining," In *SIGMOD*, 2000; and L. Sweeney, "k-anonymity: A Model for Protecting Privacy," *IJUFKS*, 10(5), 2002) until today, there is an increasing realization that subtle potential privacy breaches may arise when any regularity or structure is present in the entire collection of values considered as a single, complex data object (see, for example, H. Kargupta et al., "On the Privacy Preserving Properties of Random Data Perturbation Techniques," In *ICDM*, 2003; Z. Huang et al., "Deriving Private Information from Randomized Data," In *SIGMOD*, 2005; X. Xiao et al., "Personalized Privacy Preservation," In *SIGMOD*, 2006; and A. Machanavajjhala et al., "l-diversity: Privacy Beyond k-anonymity," In *ICDE*, 2006). The embodiments of the present invention address these challenges for time series data. They also consider true value leaks as well as filtering attempts, study the fundamental trade-offs involved in addressing both and propose a practical, effective method that is based on the wavelet transform, which has been widely successful in capturing the essential characteristics of data (see, for example, T. Li et al., "A Survey on Wavelet Applications in Data Mining," *SIGKDD Explorations*, 4(2), 2002).

Figure 17:
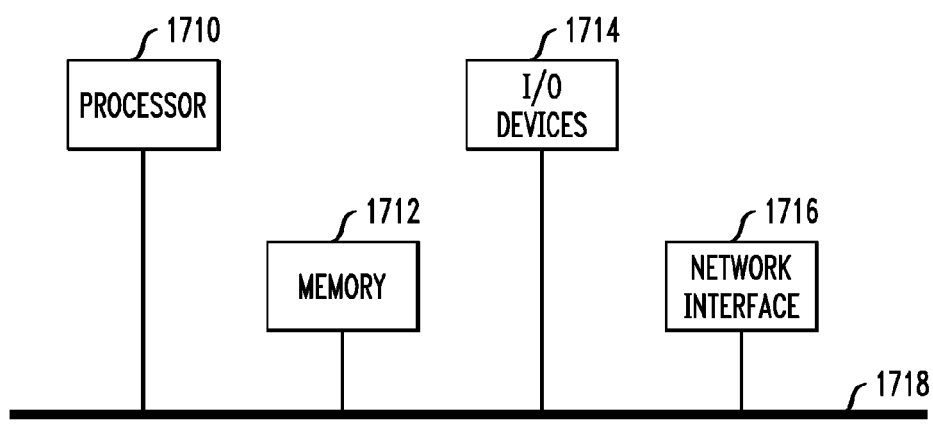
FIG. 17 is a block diagram illustrating an exemplary hardware implementation of a computing system in accordance with which one or more components/methodologies of the invention may be implemented, according to an embodiment of the present invention

Referring now to FIG. 17, a block diagram illustrates an exemplary hardware implementation of a computing system in accordance with which one or more components/methodologies of the invention (e.g., components/methodologies described in the context of FIGS. 1-10) may be implemented, according to an embodiment of the present invention.

As shown, the computer system may be implemented in accordance with a processor 1710, a memory 1712, I/O devices 1714, and a network interface 1716, coupled via a computer bus 1718 or alternate connection arrangement.

It is to be appreciated that the term "processor" as used herein is intended to include any processing device, such as, for example, one that includes a CPU (central processing unit) and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc.

In addition, the phrase "input/output devices" or "I/O devices" as used herein is intended to include, for example, one or more input devices (e.g., keyboard, mouse, scanner, etc.) for entering data to the processing unit, and/or one or more output devices (e.g., speaker, display, printer, etc.) for presenting results associated with the processing unit.

Still further, the phrase "network interface" as used herein is intended to include, for example, one or more transceivers to permit the computer system to communicate with another computer system via an appropriate communications protocol.

Software components including instructions or code for performing the methodologies described herein may be stored in one or more of the associated memory devices (e.g., ROM, fixed or removable memory) and, when ready to be utilized, loaded in part or in whole (e.g., into RAM) and executed by a CPU.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for perturbing an evolving data stream, the method comprising:
   receiving the evolving data stream;
   applying an online linear transformation to received values of the evolving data stream generating a plurality of transform coefficients;
   selecting a plurality of significant transform coefficients from the plurality of transform coefficients; and
   embedding noise into each of the plurality of significant transform coefficients, thereby perturbing the evolving data stream;

wherein the plurality of significant transform coefficients are selected for noise to be embedded therein such that a total noise variance does not exceed a defined noise variance threshold;

further wherein the receiving, applying, selecting and embedding steps are performed via a memory and at least one processor device, the processor device being operatively coupled to the memory and operative to perform the receiving, applying, selecting and embedding steps.

2. The method of claim 1, wherein, in the step of applying an online linear transformation, the online linear transformation comprises a Fourier transform.

3. The method of claim 1, wherein, in the step of applying an online linear transformation, the online linear transformation comprises a wavelet transform.

4. The method of claim 1, wherein, in the step of embedding noise, the defined noise variance threshold is predetermined by at least one of a user and application requirements.

5. The method of claim 1, wherein, in the step of embedding noise, the noise is additively embedded.

6. The method of claim 1, wherein, in the step of embedding noise, the noise is random.

7. The method of claim 1, wherein, in the step of selecting a plurality of significant transform coefficients, the plurality of significant transform coefficients comprise transform coefficients that have an absolute magnitude exceeding a defined threshold.

8. The method of claim 1, wherein, in the step of embedding noise, the noise is embedded into each significant transform coefficient in proportion to a magnitude of each significant transform coefficient.

9. Apparatus for perturbing an evolving data stream, comprising:
    a memory; and
    at least one processor coupled to the memory and operative to: (i) receive the evolving data stream; (ii) apply an online linear transformation to received values of the evolving data stream generating a plurality of transform coefficients; (iii) select a plurality of significant transform coefficients from the plurality of transform coefficients; and (iv) embed noise into each of the plurality of significant transform coefficients, thereby perturbing the evolving data stream, wherein the plurality of significant transform coefficients are selected for noise to be embedded therein such that a total noise variance does not exceed a defined noise variance threshold.

10. The apparatus of claim 9, wherein, in the operation of applying an online linear transformation, the online linear transformation comprises a Fourier transform.

11. The apparatus of claim 9, wherein, in the operation of applying an online linear transformation, the online linear transformation comprises a wavelet transform.

12. The apparatus of claim 9, wherein, in the operation of embedding noise, the defined noise variance threshold is predetermined by at least one of a user and application requirements.

13. The apparatus of claim 9, wherein, in the operation of embedding noise, the noise is additively embedded.

14. The apparatus of claim 9, wherein, in the operation of embedding noise, the noise is random.

15. The apparatus of claim 9, wherein, in the operation of selecting a plurality of significant transform coefficients, the plurality of significant transform coefficients comprise transform coefficients that have an absolute magnitude exceeding a defined threshold.

16. The apparatus of claim 9, wherein, in the operation of embedding noise, the noise is embedded into each significant transform coefficient in proportion to a magnitude of each significant transform coefficient.

17. An article of manufacture for making a computer implemented process to enable perturbing of an evolving data stream comprising the steps of:
    first computer instructions stored on a computer readable storage medium, the first computer instructions configured to receive the evolving data stream;
    second computer instructions stored on the computer readable storage medium, the second computer instructions configured to apply an online linear transformation to received values of the evolving data stream generating a plurality of transform coefficients;
    third computer instructions stored on the computer readable storage medium, the third computer instructions configured to select a plurality of significant transform coefficients from the plurality of transform coefficients; and
    fourth computer instructions stored on the computer readable storage medium, the fourth computer instructions configured to embed noise into each of the plurality of significant transform coefficients, thereby perturbing the evolving data stream, wherein the plurality of significant transform coefficients are selected for noise to be embedded therein such that a total noise variance does not exceed a defined noise variance threshold.

* * * * *